United States Patent [19]
Luteri et al.

[11] Patent Number: 5,977,024
[45] Date of Patent: Nov. 2, 1999

[54] MIXTURES AND METHODS FOR SUPPRESSING PRECIPITATION OF CHLOROACETAMIDES

[75] Inventors: George Luteri, Mount Prospect, Ill.; Raad Yacoub, Raleigh, N.C.; Charles B. Gallagher, Glencoe, Ill.; Steven Bowe, Chapel Hill, N.C.

[73] Assignee: BASF Corporation, Mt. Olive, N.J.

[21] Appl. No.: 08/963,280

[22] Filed: Nov. 3, 1997

[51] Int. Cl.⁶ .......................... A01N 25/22; A01N 43/10; A01N 37/22; A01N 37/10
[52] U.S. Cl. .......................... 504/116; 504/129; 504/139; 504/144; 504/280; 504/289; 504/324; 504/341; 504/342
[58] Field of Search .................................... 504/116, 144, 504/129, 139, 280, 289, 324, 341, 342

[56] References Cited

U.S. PATENT DOCUMENTS

| | | | |
|---|---|---|---|
| 3,013,054 | 12/1961 | Richter | 260/473 |
| 4,666,502 | 5/1987 | Seckinger et al. | 71/90 |
| 4,695,673 | 9/1987 | Heather et al. | 568/310 |
| 4,789,393 | 12/1988 | Hanagan | 71/92 |
| 5,721,191 | 2/1998 | Fenderson et al. | 504/134 |

FOREIGN PATENT DOCUMENTS

| | | |
|---|---|---|
| 230 596 | 8/1987 | European Pat. Off. |
| 315 889 | 5/1989 | European Pat. Off. |
| 338 992 | 10/1989 | European Pat. Off. |
| 380 447 | 1/1990 | European Pat. Off. |
| 394 889 | 10/1990 | European Pat. Off. |
| 461 079 | 12/1991 | European Pat. Off. |
| 549 524 | 6/1993 | European Pat. Off. |
| WO 91/10653 | 7/1991 | WIPO |

OTHER PUBLICATIONS

*Weed Control And Soil Persistence Studies With Dimethenamid In Maize*, A. Rahman and T.K. James; Proc. 45th N.Z. Plant Protection Conf. 1992: 84–88.

*Herbicidal Composition*, Kimura et al.; United States Statutory Invention Registration, Reg. No. H670, Sep. 5, 1989.

*SAN 582 H—A New Herbicide For Weed Control In Corn And Soybeans*, J. Harr, K. Seckinger, E. Ummel, Brighton Crop Protection Conference –Weeds, 1991, pp. 87–92.

*Weed Control in No–tillage and Conventional Corn (Zea mays) with ICIA–0051 and SC–0774*, John S. Wilson and Chester L. Foy; Weed Technology, 1990, vol. 4:731–738.

*Chemical Abstracts*, American Chemical Society, vol. 118, NO. 23, 228154U, Jun. 7, 1993.

U.S. Patent Application Serical No. 08/236,732, *Herbicidal Compositions*, Filed May 2, 1994.

*Primary Examiner*—S. Mark Clardy
*Attorney, Agent, or Firm*—Alston & Bird LLP

[57] ABSTRACT

The invention provides novel mixtures and methods for significantly lowering the temperature at which chloroacetamides begin to form solid precipitant, without significantly diluting the chloroacetamides.

43 Claims, No Drawings

5,977,024

MIXTURES AND METHODS FOR SUPPRESSING PRECIPITATION OF CHLOROACETAMIDES

FIELD OF THE INVENTION

The present invention relates to novel mixtures and methods having the effect of lowering the precipitation point of chloroacetamides.

BACKGROUND OF THE INVENTION

Chloroacetamides are known herbicides. More particularly, they are plant growth inhibitor herbicides which primarily inhibit growth of roots and shoots of seedlings. Examples of chloroacetamide herbicides are alachlor, metolachlor, acetochlor, metazachlor, diethatyl, propachlor and thiophenamines. An example of a known thiophenamine plant growth inhibitor herbicide is dimethenamid, whose chemical name is 2-chloro-N-(2,4-dimethyl-3-thienyl)-N-(2-methoxy-1-methylethyl)-acetamide. Processes for its production, herbicidal compositions containing it and its use as a herbicide are described in U.S. Pat. No. 4,666,502, the contents of which are incorporated herein by reference. Dimethenamid consists of 4 stereoisomers as diastereomeric mixtures (1S, aRS (known as S-dimethenamid) and 1R, aRS (known as R-dimethenamid)) and as a racemic mixture (1RS, aRS). References herein to chloroacetamides, including dimethenamid, refer to their various forms, including their various stereoisomers, unless stated otherwise.

One commercial dimethenamid product is available under the registered trademark FRONTIER® (BASF AG, Germany), with either G.0 lb/gal. or 7.5 lb/gal. dimethenamid, along with other inert ingredients, such as petroleum distillates, xylene or xylene range aromatic solvents.

While the use of, chloroacetamides, including dimethenamid, as growth inhibitor herbicides is known in the art, one drawback to their commercial use is their precipitation point—the temperature, at about standard atmospheric pressure, at which liquid chloroactamides begin to solidify to form a solid precipitant. The racemic mixture of dimethenamid has a precipitation point of about 20° C. −22° C. As a result of this property, these commercial products tend to precipitate from liquid formulations at temperatures which are common in commercial use of herbicides.

For example, the FRONTIER® product comprising 7.5 pounds of dimethenamid per gallon, tends to form a solid precipitant at temperatures of 12–13° C. and below. The temperatures experienced by these formulations during normal distribution and field application commonly drop to temperatures well below 12–13° C., thus resulting in formation of dimethenamid precipitant. This is problematic to commercial users because, among other things, precipitation inhibits the users' ability to uniformly apply the herbicide to crops. Thus, commercial users typically must heat the dimethenamid products prior to use, which can be costly and time consuming. Alternatively, manufactures of dimethenamid products are required to rotate stock of dimethenamid in heated storage with unused dimethenamid at the commercial users' facilities that has been exposed to temperatures below 120°–13° C.

It is well known that the temperature at which a dissolved liquid freezes, or precipitates, can be lowered by decreasing the mole fraction of the solute in solution of the liquid solvent. The extent to which the precipitation temperature is affected is generally directly proportional to the extent to which the mole fraction of the solvent has been decreased.

If a solution is an "ideal" solution, the extent to which the precipitation temperature decreases by addition of a solute is not affected by the composition of the solvent or solute, and a curve made by plotting precipitation temperature versus concentration will not vary when different compounds are used to dilute the liquid. The term "ideal solution" refers to a solution in which little or no specific molecular interaction occurs between its components. An "ideal solution" conforms with Raoult's law.

Thus, one theoretical alternative approach to avoiding the need to heat chloroactetamide herbicides prior to use is to significantly lower the mole fraction of (i.e., dilute) the herbicide in solution. One preferred diluent known as gamma butyrolactone can be so used to lower the melting point of dimethenamid to minus twenty degrees celsius, but in order to do so, the dimethenamid in the solution must be diluted to twenty mole percent (forty five percent by weight).

However, by significantly diluting the herbicide, its effectiveness is reduced. Furthermore, significant dilution of the herbicide results in a significant increase in the amount of total product required to achieve the desired herbicidal result. This not only results in greater cost to the user based on the amount of product purchased, but also increases significantly the costs of shipping, handling and applying the product.

Extensive experimentation was conducted in attempting to lower the precipitation temperature of the chloroacetamide herbicide, dimethenamid, by combining it in solution with various substances, and lowering the temperature of the solutions incrementally while observing them for solid precipitant formation. The dimethenamid precipitation temperature for each solution was determined as the temperature, at about standard atmospheric pressure, at which the solutions yielded at least a trace of solid dimethenamid precipitant. The term "trace" is used herein to mean an amount of solid precipitant that can be detected visibly without the aid of magnification, but which cannot be measured quantitatively without the aid of magnification. If the amount of solid precipitant can be measured visibly without the aid of magnification, then it is considered to be more than a trace.

It is understood that most substances form ideal, or nearly ideal, solutions with dimethenamid, and therefore, that the melting point of dimethenamid is not depressed substantially without significant dilution of the dimethenamid. Although some compounds have a minor effect on precipitation temperature, the deviation from ideality with these substances is not significant enough to be useful, and the substances are not acceptable in commercial herbicide formulations.

Accordingly, no method of inhibiting solid precipitant growth in chloroacetamide solutions at conventional shipping, storage and application temperatures, other than unacceptable dilution, is currently available. Therefore, commercial users of chloroacetamide herbicides, such as dimethenamid, have been unable to use such liquid products, substantially free of solid precipitant, if such products have been shipped or stored at temperatures substantially below 12°–13° C., without having to heat the product to melt, or re-dissolve, the solid precipitant therein. Because known diluents can depress the precipitation point only by substantially diluting the herbicide, the users' only alternatives in those conditions have been to either use such products containing solid precipitant therein or to employ the costly and time consuming step of heating the products to melt, or re-dissolve, the solid precipitant.

SUMMARY OF THE INVENTION

It has been found surprisingly that the temperature at which the chloroacetamide herbicide, dimethenamid, forms a solid precipitant can be lowered significantly with significantly less dilution of the dimethenamid than has heretofore been available. The invention provides chloroacetamide compositions having improved low temperature stability and methods for lowering the precipitation point of chloroacetamides. The chloroacetamide precipitation temperature is lowered by combining chloroacetamides with chemical compounds of the following formula:

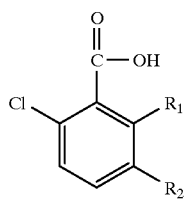

Wherein $R_1$ is either chlorine or methoxy, and $R_2$ is, optionally, hydrogen, halogen, or a lower alkyl, a lower alkyl ether, or a lower alkyl halide.

According to one preferred embodiment of the invention, a herbicidal mixture comprises a herbicidally effective amount of dimethenamid and 3,6-dichloro-2-methoxybenzoic acid, known as dicamba acid, wherein the molar concentration of the dicamba acid is from 30% to 50% of the total molar concentration of the dimethenamid and dicamba acid. The mixture can also be diluted with known inert ingredients, such as gamma butyrolactone, petroleum distillates, xylene or xylene range aromatic solvents, to adjust the concentration of herbicidal components thereof.

BRIEF DESCRIPTION OF THE DRAWING

In the drawing which forms a portion of the original disclosure of the invention:

FIG. 1 is a graph depicting precipitation point of dimethenamid at various molar concentrations in combination with dicamba and with gamma butyrolactone.

DESCRIPTION OF THE PREFERRED EMBODIMENTS

In the following detailed description, preferred embodiments of the invention are described to enable practice of the invention. Although specific terms are used to describe and illustrate the preferred embodiments, such terms are not intended as limitations on practice of the invention. Moreover, although the invention is described with reference to the preferred embodiments, numerous variations and modifications of the invention will be apparent to those of skill in the art upon consideration of the foregoing and the following detailed description.

The compositions of the invention include a herbicidally effective amount of a chloroacetamide, such as alachlor, metolachlor, acetochlor, metazachlor, diethatyl, propachlor or thiophenamines such as dimethenamid, combined with a precipitation point lowering agent. These are prepared in a ratio of from about 1:1 chloroacetamide to precipitation point lowering agent, on a mole/mole basis, up to about 2.5:1, with a preferred ratio being about a 3:2 ratio.

In accord with the invention, the precipitation point lowering agents are compounds having the following chemical formula:

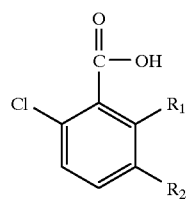

wherein $R_1$ is either chlorine or methoxy, and $R_2$ is, optionally, hydrogen, halogen, a lower alkyl, a lower alkyl ether, or a lower alkyl halide. Examples of such precipitation point lowering compounds include dicamba acid (3,6-dichloro-2-methoxybenzoic acid) and 2,6-dichlorobenzoic acid. Dicamba is a known plant growth regulator herbicide, which is commonly used in post-emergence herbicidal control of broad-leaf weeds in monocot crops. One commercially available dicamba product is known as BANVEL® (BASF AG, Germany), which contains 4.0 lb/gal. of dicamba acid in inert diluents.

Although dicamba acid and other benzoic acids are known herbicidal plant growth regulators, they have not heretofore been combined with chloroacetamides, such as dimethenamid, in accordance with the ratios of the present invention and have not achieved the precipitation point lowering effects of the present invention.

Mixtures of these compounds with the chloroacetamide herbicide dimethenamid within the parameters of the above ratios exhibit surprisingly low precipitation temperatures, enabling the temperatures of such solutions to be lowered to below –20° C. before a trace of solid precipitant is observed. Also, when temperatures of these solutions were lowered to a point where precipitation occurred, the amount of solid precipitant formed was much less, and formed much slower, than when dimethenamid is combined with other known diluents.

Infrared spectra for mixtures of dimethenamid and dicamba reveal a shift in the carbonyl bands of both dimethenamid and dicamba, as compared with infrared spectra of unmixed dimethenamid and dicamba. Furthermore, both substances, when in stoichiometric excess of the other, exhibited both shifted and non-shifted carbonyl bands, suggesting some chemical bonding in relation to the carbonyl components of the two substances. However, testing of mixtures of dimethenamid and dicamba with thin layer chromatography showed that the two substances are easily separated thereby. This demonstrates that no covalent bond is formed between dimethenamid and dicamba, and that the association between the two substances is fairly weak and dynamic.

Interestingly, in determining precipitation temperatures for solutions containing varying amounts of dicamba and of 2,6-dichlorobenzoic acid mixed with dimethenamid, it was learned that dicamba and 2,6-dichlorobenzoic acid are soluble in dimethenamid up to molar concentrations about equal to the molar concentration of dimethenamid. When the molar concentration of dicamba or 2,6-dichlorobenzoic acid exceeds that of dimethenamid, the dicamba or 2,6-dichlorobenzoic acid precipitates and requires significant heating to return to the solution.

To determine whether the anomalous precipitation temperature depression in dimethenamid is attributable to the benzoic acid structure of these compounds, solubilities of other structurally similar benzoic acids in dimethenamid were measured. Surprisingly, structurally similar benzoic acids, such as 3,5-dicamba acid, are much less soluble in dimethenamid than are dicamba and 2,6-dichlorobenzoic acid, suggesting a strong structural specificity in the interaction between dimethenamid and both dicamba and 2,6-dichlorobenzoic acid. It is believed that this structural specificity is found in the location of the chlorine and methoxy groups adjacent the acid group in both dicamba acid and 2,6-dichlorobenzoic acid, and that the electron affinity of these groups enhances the interaction of the acid group of those molecules with the carbonyl components of dimethenamid.

The mixtures and formulations described herein can be prepared by a manner known per se, in particular by stirring compounds and the other usual formula adjuvants into the dimethenamid while stirring and optionally while heating. In a preferred embodiment, the dimethenamid is heated to about 115° F. before adding dicamba thereto. Also, the concentration of the components can be varied by combining the mixtures, using methods known per se, in particular by stirring the compounds with known diluents.

As used herein, the term diluents means any liquid or solid agriculturally acceptable material which may be added to the components to provide a more easily or improved applicable form, or to achieve a usable or desired strength of activity. Examples are gamma butyrolactone, petroleum distillates, xylene, or xylene range aromatic solvents. On preferred embodiment of the present invention comprises about 5 pounds per gallon dimethenamid and about 1 pound per gallon dicamba with commercially known diluents such as petroleum distillates, xylene or xylene range aromatic solvents. At this concentration, the dicamba has the desired effect of lowering the precipitation temperature of dimethenamid, and the mixture has a desirable viscosity to facilitate application by commercial users.

The formulations of the present invention can also include other ingredients or adjuvants commonly employed in the art, including penetrants, surfactants, crop oils, drift control agents, defoaming agents, preservatives, wetting agents, adherents, antimicrobial agents, and the like, including mixtures thereof, as are also well known in the art and disclosed, for example, in the aforementioned U.S. Pat. No. 4,666,502.

Herbicidally acceptable additives can be added to the mixtures, using methods known per se, in particular by stirring, including other compounds having similar or complementary herbicidal activity or compounds having antidotal, fungicidal or insecticidal activity. Particular formulations, to be applied in spraying form, can contain surfactants such as wetting and dispersing agents, for example, an ethoxylated alkylphenol or an ethoxylated fatty alcohol. Also, compatibility enhancing agents, such as emulsifiers, can be used to improve compatibility of the formulations when combined by an end user, for example, with products containing water. For example, in one embodiment, the formulations of the present invention are combined with a blend of nonionic/anionic surfactants, and a phosphate ester to emulsify the formulations of the present invention in water. Moreover, the mixtures and formulations described herein can be used in various herbicidal applications as are known, per se, in the art, and as are described in the above-mentioned U.S. Pat. No. 4,666,502.

The following examples set forth the dimethenamid crystallization point lowering effects of several combinations of the present invention.

EXAMPLES

Solutions were prepared at room temperature and about standard atmospheric pressure. The solutions were then cooled to −20° C. The precipitation temperatures for the solutions of dimethenamid with dicamba were recorded as the temperature below which at least a trace of solid dimethenamid formed in the solution. The results are set forth in Table 1 below:

TABLE 1

| Dimethenamid Mole Fraction | Dimethenamid Weight Percent | Dicamba Mole Fraction | Dicamba Weight Percent | Precipitation Temperature ° C. |
|---|---|---|---|---|
| 0.938 | 95% | 0.062 | 5% | 19 |
| 0.878 | 90% | 0.122 | 10% | 17 |
| 0.820 | 85% | 0.180 | 15% | 16 |
| 0.762 | 80% | 0.238 | 20% | 12 |
| 0.706 | 75% | 0.294 | 25% | 9 (trace) |
| 0.652 | 70% | 0.348 | 30% | −20 |
| 0.598 | 65% | 0.402 | 35% | −20 |
| 0.546 | 60% | 0.454 | 40% | −20 |
| 0.495 | 55% | 0.505 | 45% | −20 |
| 0.445 | 50% | 0.555 | 50% | 81* |
| 0.396 | 45% | 0.604 | 55% | 89* |
| 0.348 | 40% | 0.652 | 60% | 94* |
| 0.301 | 35% | 0.699 | 65% | 96* |
| 0.256 | 30% | 0.744 | 70% | 100* |
| 0.211 | 25% | 0.789 | 75% | 102* |
| 0.167 | 20% | 0.833 | 80% | 104* |
| 0.124 | 15% | 0.876 | 85% | 108* |
| 0.082 | 10% | 0.918 | 90% | 110* |
| 0.040 | 5% | 0.960 | 95% | 112* |

*The solid formations at dicamba concentrations of 0.505 mole fraction, and below, were dimethenamid precipitant. Above that concentration, dicamba precipitant formed, which required significant heating to dissolve back into solution.

As shown in Table 1 above, when dicamba is present in concentrations of greater than about 0.30 mole percent (i.e., greater than 25% weight), the dimethenamid precipitation temperature is depressed significantly.

For comparison, the precipitation temperature of dimethenamid was measured in similar fashion in solutions with varying concentrations of gamma butyrolactone ("Gamma Blo"), a known diluent. The dimethenamid precipitation temperatures, in those solutions are set forth in Table 2 below:

TABLE 2

| Dimethenamid Mole Fraction | Dimethenamid Weight Percent | Gamma-Blo Mole Fraction | Gamma-Blo Weight Percent | Precipitation Temperature ° C. |
|---|---|---|---|---|
| 0.856 | 95% | 0.144 | 5% | 18 |
| 0.737 | 90% | 0.263 | 10% | 18 |
| 0.639 | 85% | 0.361 | 15% | 18 |
| 0.555 | 80% | 0.445 | 20% | 17 |
| 0.484 | 75% | 0.516 | 25% | 15 |
| 0.421 | 70% | 0.579 | 30% | 13 |
| 0.367 | 65% | 0.633 | 35% | 9 |
| 0.319 | 60% | 0.681 | 40% | 7 |
| 0.276 | 55% | 0.724 | 45% | 4 |
| 0.238 | 50% | 0.762 | 50% | −7 |
| 0.203 | 45% | 0.797 | 55% | −20 |
| 0.172 | 40% | 0.828 | 60% | −20 |
| 0.144 | 35% | 0.856 | 65% | −20 |

As shown in Table 2 above, a significantly greater amount of gamma butyrolactone is required to lower the precipitation temperature of dimethenamid, as compared with the amount of dicamba required to achieve a similar dimethenamid precipitation temperature. The amount of dicamba necessary to achieve a dimethenamid precipitation temperature of −20° C. is about 30% w— equivalent to a mole fraction of about 0.35. By comparison, the amount of gamma butyrolactone necessary to achieve a precipitation temperature of −20° C. is about 55% w—equivalent to a mole fraction of about 0.8.

The difference in precipitation temperature depression achieved with dicamba as the precipitation temperature lowering agent, in comparison to the normal depression caused by dilution of dimethenamid, is more easily seen in the graph shown in FIG. 1. In FIG. 1, the curve 1 indicates the precipitation temperature observed in solutions of dimethenamid and dicamba. As seen in FIG. 1, the precipitation temperature of dimethenamid is depressed significantly by dicamba beginning at the point where the dimethenamid mole fraction is approximately 0.70 and the dicamba mole fraction is approximately 0.30.

Line A—A indicates the approximate point at which dicamba begins to precipitate and requires significant heating to return the dicamba to the solution. The curve 2 in FIG. 1 illustrates depression of the dimethenamid precipitation temperature by dilution with gamma butyrolactone. As FIG. 1 illustrates, in order to depress the dimethenamid precipitation temperature significantly with gamma butyrolactone, the mole fraction of dimethenamid must be diluted significantly more than with dicamba. For instance, with dicamba, the mole fraction of dimethenamid at which dimethenamid has a precipitation temperature of 10° C. is approximately 0.70, whereas, with gamma butyrolactone, the mole fraction of dimethenamid at which the dimethenamid has a precipitation temperature of 10° C. is approximately 0.37. Similarly, with dicamba as the precipitation temperature lowering agent, dimethenamid has a precipitation temperature of −20° C. with a dimethenamid mole fraction of approximately 0.65. With gamma butyrolactone as a diluent, in order to lower the dimethenamid precipitation temperature to −20° C., the dimethenamid mole fraction must be lowered to approximately 0.20.

Tests of a similar protocol were conducted using combinations of dimethenamid with 2,6-dichlorobenzoic acid. The results of these tests showed a similar precipitation point suppression as was exhibited with combinations of dimethenamid with dicamba acid. The results are set forth in Table 3 below:

TABLE 3

| Dimethenamid Mole Fraction | Dimethenamid Weight Percent | 2,6-Di-Chloro- Mole Fraction | 2,6-Di-Chloro- Weight Percent | Precipitation Temperature ° C. |
|---|---|---|---|---|
| 0.929 | 95% | 0.071 | 5% | 18 |
| 0.862 | 90% | 0.138 | 10% | 16 |
| 0.797 | 85% | 0.203 | 15% | 15 |
| 0.735 | 80% | 0.265 | 20% | −20 |
| 0.675 | 75% | 0.325 | 25% | −20 |
| 0.618 | 70% | 0.382 | 30% | −20 |
| 0.563 | 65% | 0.437 | 35% | −20 |
| 0.510 | 60% | 0.490 | 40% | −20 |
| 0.458 | 55% | 0.542 | 45% | 49** |
| 0.409 | 50% | 0.591 | 50% | 71** |
| 0.362 | 45% | 0.638 | 55% | 73** |
| 0.316 | 40% | 0.684 | 60% | 91** |

TABLE 3-continued

| Dimethenamid Mole Fraction | Dimethenamid Weight Percent | 2,6-Di-Chloro- Mole Fraction | 2,6-Di-Chloro- Weight Percent | Precipitation Temperature ° C. |
|---|---|---|---|---|

**As with the precipitation temperature determination relating to dicamba, beginning at the point where the mole fraction of 2,6-dichlorobenzoic acid exceeds the mole fraction of dimethenamid, the 2,6-dichlorobenzoic acid precipitates and requires significant heating to dissolve in the dimethenamid. Also, as with dicamba, infrared spectra for mixtures of dimethenamid and 2,6-dichlorobenzoic acid reveal a shift in the carbonyl bands of both substances, further suggesting some chemical bonding in relation to the carbonyl components of the two substances.

To demonstrate the commercial utility of the precipitation temperature suppression provided by this invention, formulations of dimethenamid and dicamba acid were prepared at dimethenamid:dicamba weight ratios of 2:1 and 3:1, which correspond to mole ratios of 1.6:1 and 2.4:1, respectively. With gamma butyrolactone, a known diluent, samples of the formulations were diluted so that the concentration of total active ingredients (i.e., dimethenamid and dicamba) were 8 pounds per gallon, 7 pounds per gallon and 6 pounds per gallon.

The diluted samples, and samples of the undiluted 2:1 and 3:1 weight ratio dimethenamid to dicamba mixtures, were then cooled in 10° C. increments, seeded with solid dimethenamid and solid dicamba after each cooling increment, and observed for solid precipitant growth. At −20° C., none of the samples exhibited precipitation, even after seeding. At −30° C., four days after seeding, the undiluted samples and the 3 to 1 mixture that had been diluted to 8 pounds per gallon began to show slight traces of solid precipitant. The mixtures were then cooled to −40° C. and again seeded with solid dimethenamid and solid dicamba. Three days after seeding, the mixtures comprising 2 to 1 weight ratio of dimethenamid to dicamba showed only traces of solid dimethenamid. The mixtures comprising 3 to 1 weight ratio of dimethenamid to dicamba showed more significant solid precipitant growth.

The solutions were then heated in 1° C. increments up to a temperature of 0° C. to observe temperatures at which only a trace of the solid precipitant remained and at which all solid precipitant returned to the liquid solution. The results are shown in Table 4 below:

TABLE 4

| Weight Ratio Dimethenamid to Dicamba | Concentration After Dilution | Only Trace Solids Remaining ° C. | No Solids Remaining ° C. |
|---|---|---|---|
| 2:1 | No Dilution | N/A* | N/A* |
| 2:1 | 8 lbs/gal. | N/A** | −9 |
| 2:1 | 7 lbs/gal. | N/A** | −11 |
| 2:1 | 6 lbs/gal. | N/A** | −11 |
| 3:1 | No Dilution | −39 | N/A*** |
| 3:1 | 8 lbs/gal. | −10 | −3 |
| 3:1 | 7 lbs/gal. | −15 | −8 |
| 3:1 | 6 lbs/gal. | −16 | −12 |

*Only trace solid precipitant present at beginning of warm-up (−39° C.) and also at end of warm-up (0° C.).
**Only trace solid precipitant present at beginning of warm-up (−39° C.).
***Trace solid precipitant remained at end of warm-up (0° C.).

The invention has been described in considerable detail with reference to its preferred embodiments. However, numerous variations and modifications can be made within the spirit and scope of the invention without departing from That which is claimed is:

1. A composition suitable as a herbicide comprising a herbicidally effective amount of a chloroacetamide herbicide and a chloroacetamide precipitation temperature lowering agent, said composition comprising at least about a 40 mole percent concentration of the chloroacetamide herbicide, and said precipitation temperature lowering agent being present in a sufficient quantity that said composition is substantially free from solid chloroacetamide at a temperature less than about ten degrees celsius.

2. A composition according to claim 1, wherein said chloroacetamide herbicide is selected from alachlor, metolachlor, acetochlor, metazachlor, diethatyl, propachlor and thiophenamines.

3. A composition according to claim 1, wherein said chloroacetamide herbicide comprises a thiophenamine.

4. A composition according to claim 1, wherein said chloroacetamide herbicide comprises dimethenamid.

5. A composition according to claim 1 wherein said precipitation temperature lowering agent comprises at least one compound having the formula

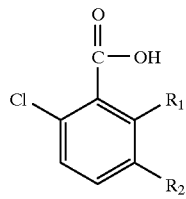

wherein $R_1$ is either chlorine or methoxy, and $R_2$ is, optionally, hydrogen, halogen, lower alkyl, lower alkyl halide, or a lower alkyl ether.

6. A composition according to claim 5 wherein said precipitation temperature lowering agent consists essentially of dicamba acid, 2,6-dichlorobenzoic acid, or combinations thereof.

7. A composition according to claim 5 wherein said precipitation temperature lowering agent comprises dicamba acid.

8. A composition according to claim 5 wherein said precipitation temperature lowering agent comprisees 2,6-dichlorobenzoic acid.

9. A composition according to claim 4 wherein said precipitation temperature lowering agent comprises at least one compound having the formula:

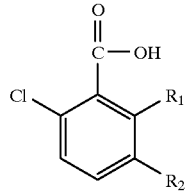

wherein $R_1$ is either chlorine or methoxy, and $R_2$ is, optionally, hydrogen, halogen, lower alkyl, lower alkyl halide, or a lower alkyl ether.

10. A composition according to claim 9 wherein said precipitation temperature lowering agent consists essentially of dicamba acid, 2,6-dichlorobenzoic acid, or combinations thereof.

11. A composition according to claim 9 wherein said precipitation temperature lowering agent comprises dicamba acid.

12. A composition according to claim 9 wherein said precipitation temperature lowering agent comprises 2,6-dichlorobenzoic acid.

13. A composition according to claim 10 wherein said precipitation temperature lowering agent is present in a sufficient quantity that said composition is substantially free from solid dimethenamid at a temperature less than about five degrees celsius.

14. A composition according to claim 10 wherein said precipitation temperature lowering agent is present in a sufficient quantity that said composition is substantially free from solid dimethenamid at a temperature less than about zero degrees celsius.

15. A composition according to claim 10 wherein said precipitation temperature lowering agent is present in a sufficient quantity that said composition is substantially free from solid dimethenamid at a temperature less than about minus ten degrees celsius.

16. A composition according to claim 10 wherein said precipitation temperature lowering agent is present in a sufficient quantity that said composition is substantially free from solid dimethenamid at a temperature less than about minus twenty degrees celsius.

17. A composition according to claim 10 wherein said precipitation temperature lowering agent is present in a sufficient quantity that said composition is substantially free from solid dimethenamid at a temperature less than about minus thirty degrees celsius.

18. A composition according to claim 10 wherein said precipitation temperature lowering agent is present in a sufficient quantity that said composition is substantially free from solid dimethenamid at a temperature less than about minus forty degrees celsius.

19. A composition suitable as a herbicide comprising a herbicidally effective amount of dimethenamid and a dimethenamid precipitation temperature lowering agent, the molar ratio of the dimethenamid to the precipitation temperature lowering agent being in a range from about 1:1 to about 2.5:1, and said composition being substantially free from crystalline dimethenamid at a temperature less than about five degrees celsius.

20. A composition according to claim 19 wherein said crystallization temperature lowering agent comprises at least one compound having the formula:

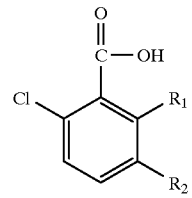

wherein $R_1$ is either chlorine or methoxy, and $R_2$ is, optionally, hydrogen, halogen, a lower alkyl, a lower alkyl halide, or a lower alkyl ether.

21. A composition according to claim 20 wherein said precipitation temperature lowering agent consists essentially of dicamba acid, 2,6-dichlorobenzoic acid, or combinations thereof.

22. A composition according to claim 20 wherein said precipitation temperature lowering agent comprises dicamba acid.

23. A composition according to claim 20 wherein said precipitation temperature lowering agent comprises 2,6-dichlorobenzoic acid.

24. A composition according to claim 20 wherein said precipitation temperature lowering agent is present in a sufficient quantity that said composition is substantially free from solid dimethenamid at a temperature less than about zero degrees celsius.

25. A composition according to claim 20 wherein said precipitation temperature lowering agent is present in a sufficient quantity that said composition is substantially free from solid dimethenamid at a temperature less than about minus ten degrees celsius.

26. A composition according to claim 20 wherein said precipitation temperature lowering agent is present in a sufficient quantity that said composition is substantially free from solid dimethenamid at a temperature less than about minus twenty degrees celsius.

27. A composition according to claim 20 wherein said precipitation temperature lowering agent is present in a sufficient quantity that said composition is substantially free from solid dimethenamid at a temperature less than about minus thirty degrees celsius.

28. A composition according to claim 20 wherein said precipitation temperature lowering agent is present in a sufficient quantity that said composition is substantially free from solid dimethenamid at a temperature less than about minus forty degrees celsius.

29. A composition according to claim 25 wherein the molar ratio of the dimethenamid to the precipitation temperature lowering agent is in a range from about 1.5:1 to about 2:1.

30. A composition according to claim 25 wherein the molar ratio of the dimethenamid to the precipitation temperature lowering agent is about 1.5:1.

31. A composition according to claim 25 further comprising an agriculturally acceptable diluent.

32. A method for forming a low-temperature storage-stable dimethenamid composition comprising combining dimethenamid with a dimethenamid precipitation temperature lowering agent and with from 0 mole percent to about 50 mole percent of an agriculturally acceptable diluent, to form a composition having a molar concentration of dimethenamid of greater than about 40 mole percent based on the total amount of said dimethenamid, precipitation temperature lowering agent, and diluent in said composition, said precipitation temperature lowering agent being present in a quantity sufficient that said composition is substantially free from solid dimethenamid at a temperature less than about zero degrees celsius.

33. A method according to claim 32 wherein said precipitation temperature lowering agent is present in a quantity sufficient that said composition is substantially free from solid dimethenamid at a temperature less than about minus ten degrees celsius.

34. A method according to claim 32 wherein said precipitation temperature lowering agent is present in a quantity sufficient that said composition is substantially free from solid dimethenamid at a temperature less than about minus twenty degrees celsius.

35. A method according to claim 32 wherein said precipitation temperature lowering agent is present in a quantity sufficient that said composition is substantially free from solid dimethenamid at a temperature less than about minus thirty degrees celsius.

36. A method according to claim 32 wherein said precipitation temperature lowering agent is present in a quantity sufficient that said composition is substantially free from solid dimethenamid at a temperature less than about minus forty degrees celsius.

37. A method according to claim 32 wherein said precipitation temperature lowering agent comprises at least one compound having the formula:

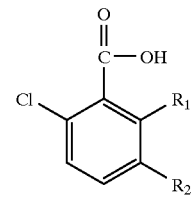

wherein $R_1$ is either chlorine or methoxy, and $R_2$ is, optionally, hydrogen, halogen, or a lower alkyl ether.

38. A method according to claim 37 wherein said precipitation temperature lowering agent consists essentially of dicamba acid, 2,6-dichlorobenzoic acid, or combinations thereof.

39. A method according to claim 37 wherein said crystallization temperature lowering agent comprises dicamba acid.

40. A method according to claim 37 wherein said crystallization temperature lowering agent comprises 2,6-dichlorobenzoic acid.

41. A method according to claim 37 wherein the concentration of the precipitation temperature lowering agent in said composition is less than about 40 mole percent based on the total amount of said dimethenamid, precipitation temperature lowering agent, and diluent in said composition.

42. A method for forming a low-temperature storage-stable dimethenamid composition comprising combining dimethenamid with from about 30 mole percent and about 50 mole percent dicamba and from 0 mole percent to about 50 mole percent of an agriculturally acceptable diluent, to form a composition having a molar concentration of dimethenamid of greater than about 40 mole percent based on the total amount of said dimethenamid, dicamba and diluent in said composition, said dicamba being present in a quantity sufficient that said composition is substantially free from solid dimethenamid at a temperature less than about minus twenty degrees celsius.

43. A method for forming a low-temperature storage-stable dimethenamid composition comprising combining dimethenamid with from about 30 mole percent and about 50 mole percent 2,6-dichlorobenzoic acid and from 0 mole percent to about 50 mole percent of an agriculturally acceptable diluent, to form a composition having a molar concentration of dimethenamid of greater than about 40 mole percent based on the total amount of said dimethenamid, 2,6-dichlorobenzoic acid and diluent in said composition, said 2,6-dichlorobenzoic acid being present in a quantity sufficient that said composition is substantially free from solid dimethenamid at a temperature less than about minus twenty degrees celsius.

* * * * *

UNITED STATES PATENT AND TRADEMARK OFFICE
CERTIFICATE OF CORRECTION

PATENT NO. : 5,977,024
DATED : Nov. 2, 1999
INVENTOR(S) : Luteri et al.

It is certified that error appears in the above-identified patent and that said Letters Patent is hereby corrected as shown below:

The title page, should be deleted to be replaced with the attached title page.

On title page, after [57] ABSTRACT, "43 Claims, No Drawings" should read --43 Claims, 1 Drawing Sheet--

In the drawings, figure 1 should appear as per attached.

Title page, [56] References Cited, OTHER PUBLICATIONS, line 13, "NO." should read--No.--;line 14, "Serical" should read --Serial--.

Signed and Sealed this

Fourth Day of July, 2000

*Attest:*

Q. TODD DICKINSON

*Attesting Officer*   *Director of Patents and Trademarks*

UNITED STATES PATENT AND TRADEMARK OFFICE
CERTIFICATE OF CORRECTION

PATENT NO. : 5,977,024
DATED : November 2, 1999
INVENTOR(S) : Luteri et al.

It is certified that error appears in the above-identified patent and that said Letters Patent is hereby corrected as shown below:

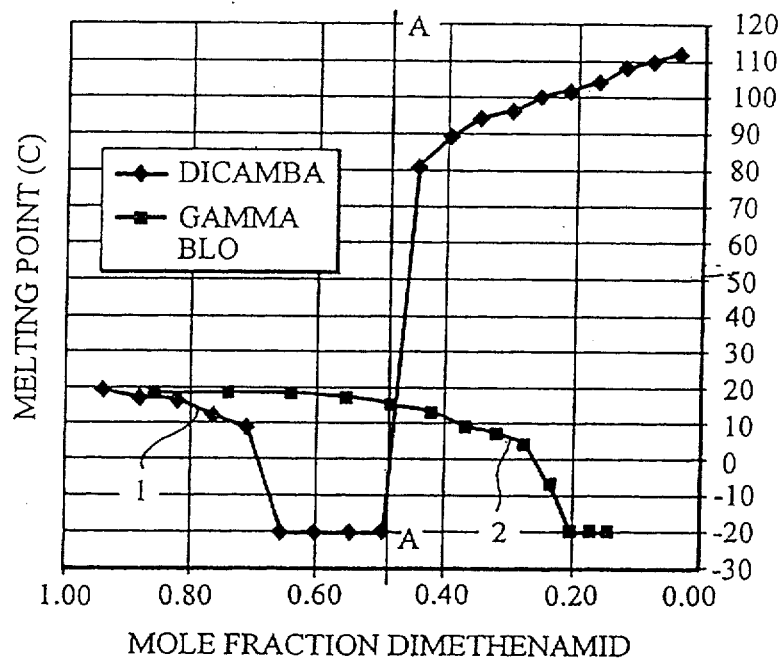

FIG. 1

United States Patent [19]
Luteri et al.

[11] Patent Number: 5,977,024
[45] Date of Patent: Nov. 2, 1999

[54] MIXTURES AND METHODS FOR SUPPRESSING PRECIPITATION OF CHLOROACETAMIDES

[75] Inventors: George Luteri, Mount Prospect, Ill.; Raad Yacoub, Raleigh, N.C.; Charles B. Gallagher, Glencoe, Ill.; Steven Bowe, Chapel Hill, N.C.

[73] Assignee: BASF Corporation, Mt. Olive, N.J.

[21] Appl. No.: 08/963,280

[22] Filed: Nov. 3, 1997

[51] Int. Cl.$^6$ ............ A01N 25/22; A01N 43/10; A01N 37/22; A01N 37/10

[52] U.S. Cl. ............ 504/116; 504/129; 504/139; 504/144; 504/280; 504/289; 504/324; 504/341; 504/342

[58] Field of Search ............ 504/116, 144, 504/129, 139, 280, 289, 324, 341, 342

[56] References Cited

U.S. PATENT DOCUMENTS

| | | | |
|---|---|---|---|
| 3,013,054 | 12/1961 | Richter | 260/473 |
| 4,666,502 | 5/1987 | Seckinger et al. | 71/90 |
| 4,695,673 | 9/1987 | Heather et al. | 568/310 |
| 4,789,393 | 12/1988 | Hanagan | 71/92 |
| 5,721,191 | 2/1998 | Fenderson et al. | 504/134 |

FOREIGN PATENT DOCUMENTS

| | | |
|---|---|---|
| 230 596 | 8/1987 | European Pat. Off. |
| 315 889 | 5/1989 | European Pat. Off. |
| 338 992 | 10/1989 | European Pat. Off. |
| 380 447 | 1/1990 | European Pat. Off. |
| 394 889 | 10/1990 | European Pat. Off. |
| 461 079 | 12/1991 | European Pat. Off. |
| 549 524 | 6/1993 | European Pat. Off. |
| WO 91/10653 | 7/1991 | WIPO |

OTHER PUBLICATIONS

*Weed Control And Soil Persistence Studies With Dimethenamid In Maize*, A. Rahman and T.K. James; Proc. 45th N.Z. Plant Protection Conf. 1992: 84–88.

*Herbicidal Composition*, Kimura et al.; United States Statutory Invention Registration, Reg. No. H670, Sep. 5, 1989.

*SAN 582 H—A New Herbicide For Weed Control In Corn And Soybeans*, J. Harr, K. Seckinger, E. Ummel, Brighton Crop Protection Conference –Weeds, 1991, pp. 87–92.

*Weed Control in No–tillage and Conventional Corn (Zea mays) with ICIA–0051 and SC–0774*, John S. Wilson and Chester L. Foy; Weed Technology, 1990, vol. 4:731–738.

*Chemical Abstracts*, American Chemical Society, vol. 118, NO. 23, 228154U, Jun. 7, 1993.

U.S. Patent Application Serical No. 08/236,732, *Herbicidal Compositions*, Filed May 2, 1994.

*Primary Examiner*—S. Mark Clardy
*Attorney, Agent, or Firm*—Alston & Bird LLP

[57] ABSTRACT

The invention provides novel mixtures and methods for significantly lowering the temperature at which chloroacetamides begin to form solid precipitant, without significantly diluting the chloroacetamides.

43 Claims, No Drawings

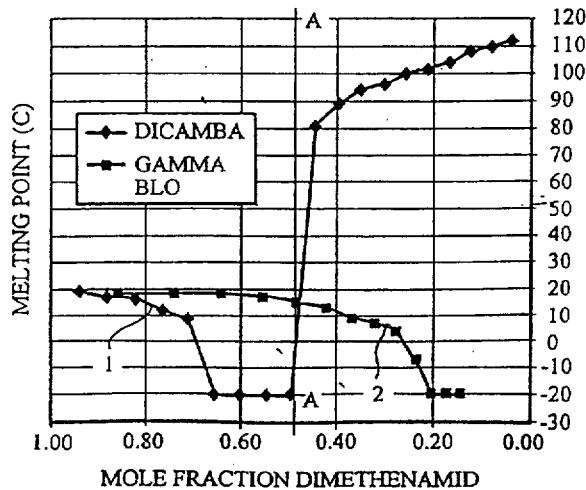

DIMETHENAMID MELTING POINT PHASE DIAGRAM